(12) United States Patent
Verhoef et al.

(10) Patent No.: US 7,761,164 B2
(45) Date of Patent: Jul. 20, 2010

(54) COMMUNICATION SYSTEM FOR MEDICAL DEVICES

(75) Inventors: William D. Verhoef, Andover, MN (US); Gregory J. Haubrich, Champlin, MN (US); Javaid Masoud, Shoreview, MN (US); Len D. Twetan, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 696 days.

(21) Appl. No.: 11/290,387

(22) Filed: Nov. 30, 2005

(65) Prior Publication Data

US 2007/0123955 A1 May 31, 2007

(51) Int. Cl.
*A61N 1/362* (2006.01)

(52) U.S. Cl. .............................. 607/30; 607/32; 607/60; 128/903; 128/904

(58) Field of Classification Search ................... 607/29, 607/32, 60; 128/903, 904; 705/2; 455/571–574
See application file for complete search history.

(56) References Cited

U.S. PATENT DOCUMENTS

| 6,804,558 B2 * | 10/2004 | Haller et al. .................. 607/30 |
| 2003/0104849 A1 * | 6/2003 | Arimitsu ..................... 455/574 |
| 2004/0059392 A1 * | 3/2004 | Parramon et al. ............. 607/36 |
| 2004/0117204 A1 | 6/2004 | Mazar et al. |

FOREIGN PATENT DOCUMENTS

| WO | 01/43631 A1 | 6/2001 |
| WO | 02/34331 A2 | 5/2002 |
| WO | 02/067122 A1 | 8/2002 |
| WO | WO02067122 A1 | 8/2002 |
| WO | 03/095024 A2 | 11/2003 |

OTHER PUBLICATIONS

International Search Report for corresponding International Application No. PCT/US2006/060585, mailed Aug. 24, 2007.
Written Opinion from corresponding PCT Application Serial No. PCT/US2006/060585 dated May 31, 2008, 8 pages.
International Preliminary Report on Patentability from corresponding PCT Application Serial No. PCT/US2006/060585 dated Jun. 3, 2008, 9 pages.

* cited by examiner

*Primary Examiner*—Carl H Layno
*Assistant Examiner*—Gary A Porter, Jr.
(74) *Attorney, Agent, or Firm*—Stephen W. Bauer; Michael J. Ostrom

(57) ABSTRACT

A communications device facilitates communication between a medical device and a wireless communications network and comprises a telemetry circuit configured to wirelessly communicate with one or more medical devices, and a computer network communication interface configured to wirelessly communicate directly with a wireless computer network. The communications device also comprises a peripheral device communication interface configured to communicate with a wireless peripheral device and a processor being in operable communication with, and configured to control operations of, the telemetry circuit, the network communication interface, and the peripheral device communication interface.

22 Claims, 5 Drawing Sheets

US 7,761,164 B2

COMMUNICATION SYSTEM FOR MEDICAL DEVICES

FIELD OF THE INVENTION

The present invention generally relates to implantable, body-worn, or external medical devices and, more particularly, to a system and method for providing improved communication capability between such medical devices and a remote communication system and/or health care provider.

BACKGROUND OF THE INVENTION

Various types of medical devices have been developed for providing therapy, diagnostics, and/or patient monitoring. Certain ones of these devices are configured for implantation within the patient's body and are typically referred to as implantable medical devices or IMDs. Others may be worn on the patient's exterior. Many of these medical devices include various amounts of electronic memory for storing device operating and control software, and various types of patient- and device-related data. In addition, some of these same medical devices may include signal processing and telemetry circuitry, that allows some or all of the data stored in the memory to be transmitted to a remote computer network or other communication node. The device may also receive and store data transmitted to it remotely from a computer network or other communication node.

The performance of such a medical device and the status of the patient's health may be assessed by retrieving device-related data and patient-related data from the medical device. In addition, it may be necessary to periodically update the software in the medical device. Data may be retrieved and/or updated software installed by having the patient visit a hospital or clinic, retrieving the stored data and/or installing the updated software by means of a programmer or other device. Depending on the frequency at which data retrieval or software updates occurs, this procedure can be difficult and inconvenient for certain patients, most notably for those that live in remote areas or those that may have limited physical mobility. Thus, various remote sensing and communication systems and methods have been developed to address these drawbacks.

Nonetheless, the need still exists for an easier, faster, and more cost-effective system for monitoring and controlling the performance of some medical devices and for assessing patient health on a regular and/or continuous basis that does not require patient presence at a health care facility. The present invention addresses at least this need.

BRIEF SUMMARY OF THE INVENTION

The present invention relates to a system for facilitating communication between a medical device and a wireless communications network, which comprises a telemetry circuit configured to wirelessly communicate with one or more medical devices. A computer network communication interface is configured to wirelessly communicate directly with the wireless computer network, and a peripheral device communication interface is configured to communicate with a wireless peripheral device. A processor is in operable communication with, and configured to control operations of, the telemetry circuit, the network communication interface, and the peripheral device communication interface.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary and is not intended to limit the invention or the application and uses of the invention. Furthermore, there is no intention to be bound by any theory presented in the preceding background of the invention or the following detailed description of the drawings. In this regard, before proceeding with the detailed description, it is to be appreciated that the described embodiment is not limited to use in conjunction with a specific type of medical device. Thus, although the present embodiment is, for convenience of explanation, depicted and described as being implemented in an implantable cardioverter-defibrillator (ICD), it will be appreciated that it can be implemented in various other medical device types.

Figure 1:
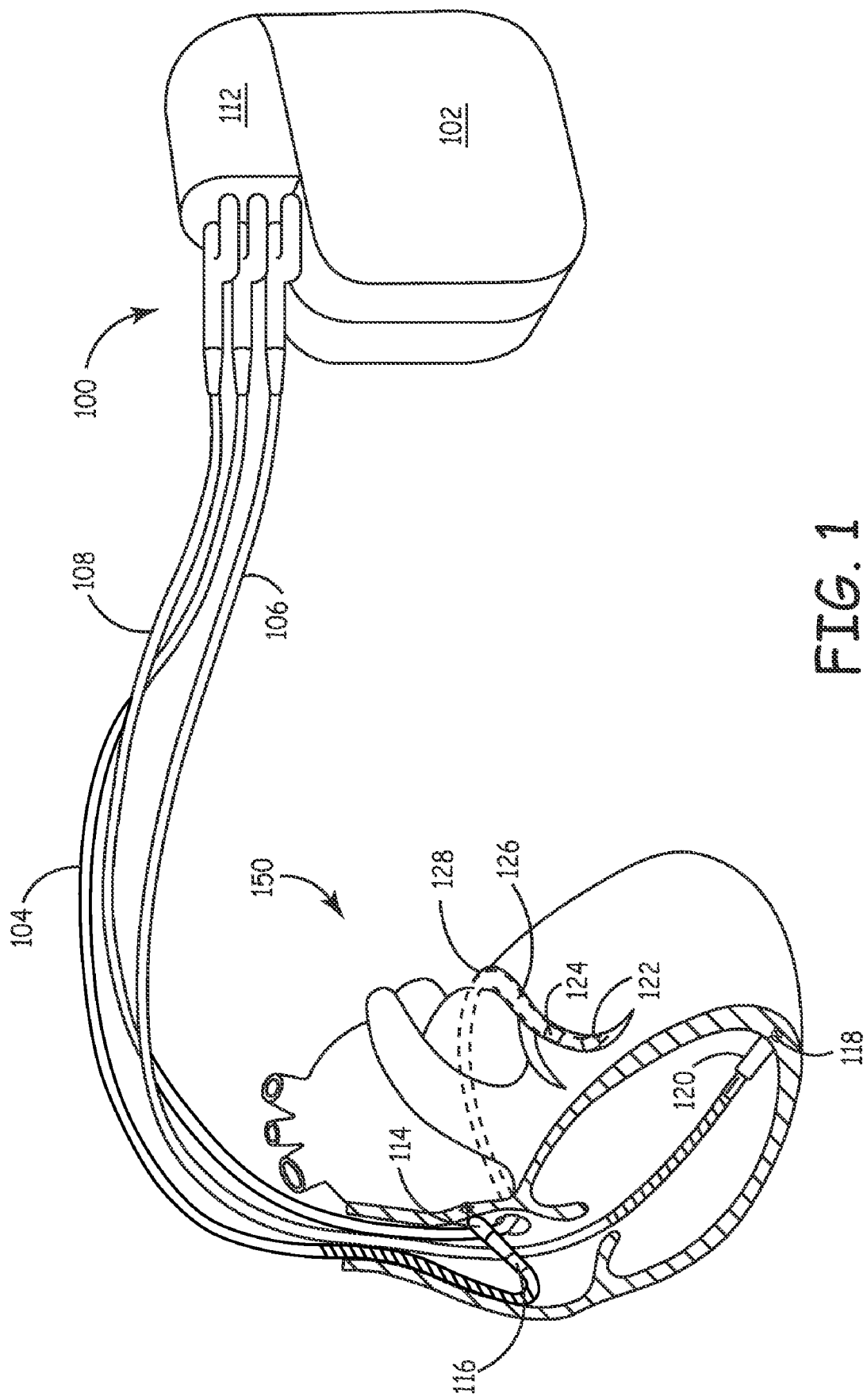
FIG. 1 is a perspective view of an implantable cardioverter defibrillator coupled to a heart and which is exemplary of one type of implantable medical device that may incorporate an embodiment of the present invention.

Referring to FIG. 1, a simplified representation of an ICD 100 and its connection to a patient heart 150 is depicted. The ICD 100 includes a housing 102 and a plurality of leads, including a first lead 104, a second lead 106, and a third lead 108. The housing 102 is preferably formed of a suitable, internal body compatible material that has been approved for medical use, such as, for example, titanium. The housing 102 is preferably hermetically sealed, so that it is substantially impervious to body fluids, and is suitably physiologically shaped to substantially avoid any sharp edges, so that tissue damage during and after implantation can be substantially avoided. The housing 102 includes a connector header 112, which includes separate connector ports and feedthroughs (neither are shown), at least one for each lead 104-108. The connector ports each electrically couple one of the leads 104-108 to one of the feedthroughs, which in turn electrically couples the connector port to the associated circuitry housed within the housing 102. A detailed description of at least a portion of this circuitry is provided further below.

The first, second, and third leads 104-108, each of which include a plurality of electrodes, extend subcutaneously from the housing 102 and include a plurality of electrodes that can be used for pacing, sensing, and/or cardioversion/defibrillation. When implanted in a patient, the first lead 104 extends into the right atrial chamber of the heart 150, where it is coupled to the right atrial wall. In the depicted embodiment, the first lead 104 is implemented as a bipolar endocardial lead and includes an atrial tip (ATIP) pace/sense electrode 114 and an atrial ring (ARING) pace/sense electrode 116. During cardiac pacing operations, cardiac pacing pulses are delivered, and atrial depolarization events are sensed, between the atrial tip and atrial ring pace/sense electrodes 114 and 116. It will be appreciated that in an alternative embodiment, the first lead 104 could be implemented as a unipolar endocardial lead. In such an alternative embodiment, the housing 102 would function as one of the atrial pace/sense electrodes.

The second lead 106 extends through the right atrial chamber of the heart 150 and into the right ventricle, where it is coupled to the right ventricle wall. In the depicted embodiment, the second lead 106 is implemented as a bipolar endocardial lead and includes a right ventricle tip (RVTIP) pace/sense electrode 118 and a right ventricle ring (RVRING) pace/sense electrode 120. During cardiac pacing operations, cardiac pacing pulses are delivered, and right ventricular depolarization events are sensed, between the right ventricular tip and right ventricular ring pace/sense electrodes 118 and 120. As with the first lead 104, it will be appreciated that the second lead 106 could alternatively be implemented as a unipolar endocardial lead, rather than as a bipolar lead.

The third lead 108, similar to the second lead 106, passes through the right atrial chamber of the heart 150. However, rather than extending into the right ventricle, the third lead 108 extends through the coronary sinus, and into the great vein 128 proximate the left ventricle of the heart 150. In the depicted embodiment, the third lead 108 is also implemented as a bipolar endocardial lead, and thus includes a left ventricle tip (LVTIP) pace/sense electrode 122, a left ventricle ring (LVRING) pace/sense electrode 124, and a right ventricle coil (LVCOIL) electrode 126. During cardiac pacing operations, cardiac pacing pulses are delivered, and left ventricular depolarization events are sensed, between the left ventricular tip and left ventricular ring pace/sense electrodes 122 and 124. In the depicted embodiment, left ventricular pace pulses and/or ventricular depolarization events may also be delivered and/or sensed between the left ventricular ring pace/sense electrode 124 and the right ventricular coil electrode 126. As with the first and second leads 104 and 106, it will be appreciated that the third lead 108 could alternatively be implemented as a unipolar endocardial lead, rather than as a bipolar lead.

In describing the depicted ICD 100 above, each of the "pace/sense" electrodes were described as preferably implementing both pacing and sensing functions. It will nonetheless be appreciated that the pace/sense electrodes may be implemented exclusively as pace or sense electrodes, or may be implemented in programmed combinations for sensing cardiac signals and delivering cardiac pacing pulses along programmed pacing and sensing vectors. It will additionally be appreciated that the ICD 100 may be used to deliver cardioversion-defibrillation shocks may be applied, when needed, between selected pairs of the electrodes 114-126, according to any one of numerous defibrillation regimens.

Figure 2:
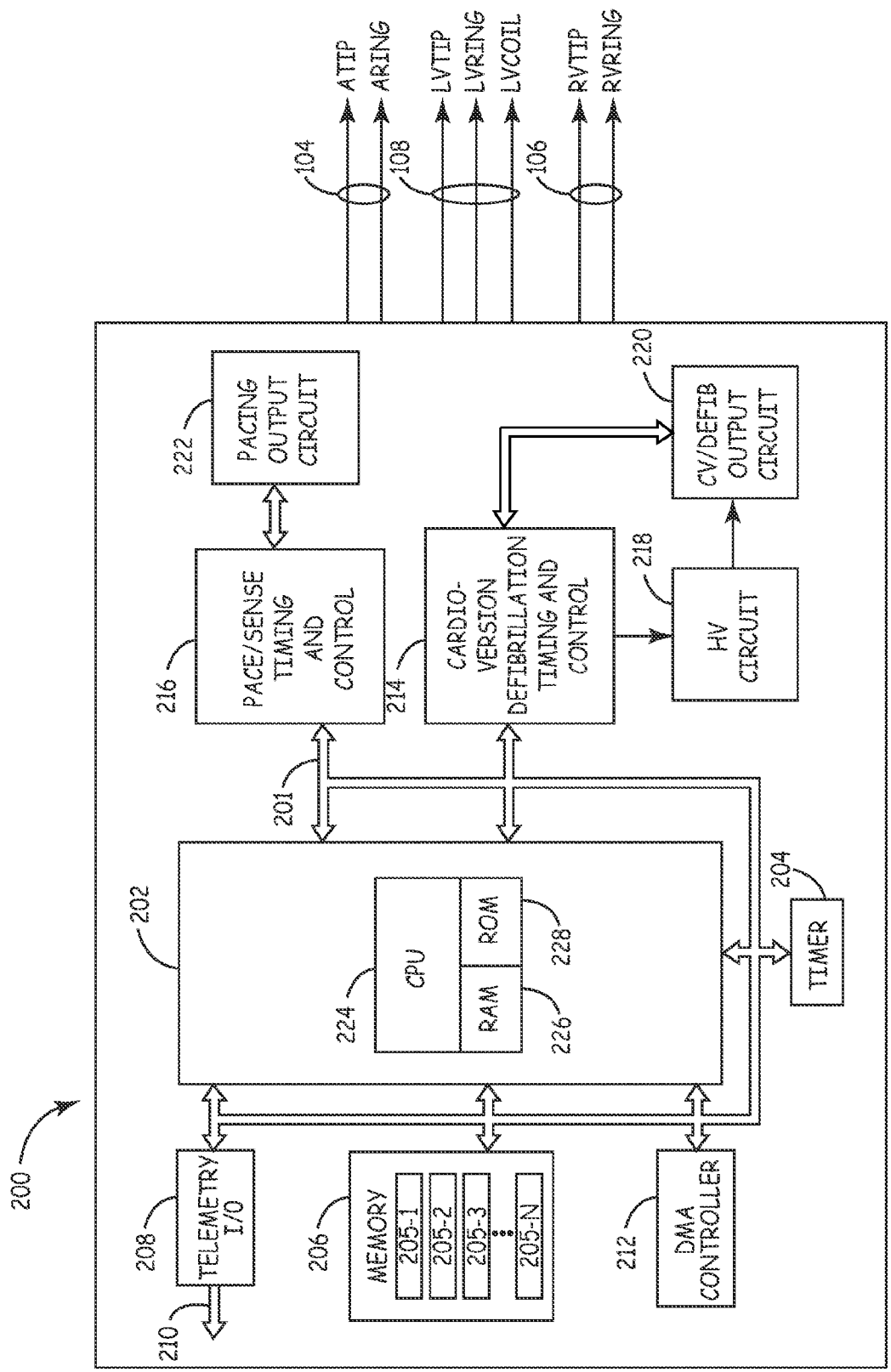
FIG. 2 is a functional block diagram of an exemplary circuit architecture that may be included in the medical device of FIG. 1.

As was noted above, the ICD 100 includes circuitry within the housing 102 that is used to control the overall operation of the ICD 100. At least a portion of this circuitry is depicted in FIG. 2, and will now be described in more detail. The circuitry 200 depicted in FIG. 2 includes a controller circuit 202 and various other functional circuit blocks 204-218 that are in operable communication with, and which may be operated under control of, the controller circuit 202 via, for example, a common communications data bus 201. It will be appreciated that the circuitry depicted in FIG. 2 is merely exemplary of a particular architecture, and that numerous other circuit architectures may be used to implement the operation of the ICD 100. The controller circuit 202 includes, among other things, a CPU (central processing unit) 224, which may include on-board RAM (random access memory) 226, and on-board ROM (read only memory) 228. The CPU 224 may be any one of numerous known general purpose processors or an application specific processor that operates in response to program instructions. Such program instructions may be stored in either or both the RAM 226 and the ROM 228. For example, the operating system software may be stored in the ROM 228, whereas various operating mode software routines and various operational parameters may be store in the RAM 226. It will be appreciated that this is merely exemplary of one scheme for storing operating software and software routines, and that various other storage schemes may be implemented. It will also be appreciated that the controller circuit 202 may be implemented using various other circuits, not just a programmable processor. For example, digital logic circuits and analog signal processing circuits could also be used.

A clock/timer circuit 204 provides one or more clock and timing signals to the controller circuit 202 and, if needed, to various ones of the other functional blocks 206-218. The clock and timing signals provide for the proper synchronous operation of the various functional circuits that make up the circuitry 200. The clock/timer circuit 204 may be any one of numerous known circuits for providing clock and/or timing signals. Non-limiting examples include various types of crystal oscillators, such as a temperature compensated crystal oscillator (TXCO), a micro-computer compensated crystal oscillator (MCXO), and an oven controlled crystal oscillator (OCXO).

A memory circuit 206 is in operable communication with the controller circuit 202 via the communications data bus 201. The memory circuit 206 includes a plurality of memory registers 205-1, 205-2, 205-2, . . . 205-N, in which various types of data are stored. The data that the memory circuit 206 stores in its memory registers 205 may include both device-related data and physiological-related data. It will be appreciated that one or more memory circuits 206 may be in operable communication with the controller circuit 202 to store such data. It will also be appreciated that the memory circuit 206 could be integrally formed as part of the controller circuit 202 and/or CPU 224, RAM 226, and/or ROM 228, or could be part of a device or system that is physically separate from the ICD 100. The data that may be stored in memory circuit 206 include, but are not limited to, various types of patient-related data, and various types of device-related data.

Some or all of the data stored in the memory circuit 206 may be read and transmitted to an external communication device (not shown in FIG. 2). Moreover, data may be received from an external communication device and written into the memory circuit 206. To implement this functionality, the ICD circuitry 200 includes a telemetry input/output (I/O) circuit 208 and an antenna 210. The telemetry I/O circuit 208 is coupled to the antenna 210 and, as its name connotes, functions as an input device, or receiver, when the antenna 210 is receiving data transmitted to the ICD 100, and functions as an output device, or transmitter, when data are being transmitted from the ICD 100. The data transmitted to and from the ICD 100 is done so using radio frequency (RF) waves. Thus, the telemetry I/O circuit 208 includes one or more RF signal sources that may be used to demodulate the data received by the ICD 100, and to modulate the data being transmitted by the ICD 100. The telemetry I/O circuit 208 may also function to decode interrogation signals it receives from an external communication device and transfer these decoded signals to the controller circuit 202. The controller circuit 202 may then appropriately command the telemetry I/O circuit 208 to be configured to transmit or receive data.

In the depicted embodiment, a DMA (direct memory access) controller 212 is in operable communication with the controller circuit 202. The DMA controller 212, as is generally known, provides direct memory access to memory circuit memory registers 205, or to the RAM 226 or ROM 228, without involving the CPU 224. This can conserve battery power and simplify data read and write operations. It will be appreciated that the DMA controller 212 could be omitted or could form an integral part of the controller circuit 220.

A cardioversion/defibrillation timing and control circuit 214 and a pace/sense timing and control circuit 216 are each coupled to the controller circuit 202 via the communications data bus 201. The cardioversion/defibrillation timing and control circuit 214, in response to instructions from the controller circuit 202, controls the operations of a high voltage (HV) circuit 218 and a cardioversion/defibrillation output circuit 220 to deliver cardioversion/defibrillation shock therapy pulses when needed such as, for example, in the event an atrial or ventricular fibrillation or flutter, or a malignant high rate tachycardia, is detected. The high voltage circuit 218 stores and supplies relatively high voltage energy using, for example, a non-illustrated charging circuit to charge one or more non-illustrated high voltage capacitors to a relatively high voltage. The cardioversion/defibrillation output circuit 220 includes a plurality of high voltage switches (not shown) that deliver the shock therapy pulses to selected ones of the depicted electrodes 114-126 and/or other non-illustrated electrodes. The cardioversion/defibrillation output circuit 220, in response to the cardioversion/defibrillation timing and control circuit 214, determines whether a monophasic or biphasic therapy pulses are delivered.

The pace/sense timing and control circuit 216 is programmable and, in response to instructions from the controller circuit 202, controls a pacing output circuit 222 to deliver cardiac pacing pulses to the heart 150 in accordance with any one of numerous atrial and ventricular pacing operational modes. The pace/sense timing and control circuit 216, together with the pacing output circuit 222, may also implement various tachyarrhythmia detection and classification operations. The pacing output circuit 222, like the cardioversion/defibrillation output circuit 220, includes a plurality of switches, which are not shown in FIG. 2, that deliver the shock therapy pulses to selected ones of the depicted electrodes 114-126. The pacing output circuit 222 additionally includes a pacing energy supply circuit, which is also not shown in FIG. 2. The pacing energy supply circuit stores and supplies the electrical energy that is delivered to the selected electrodes 114-126 as cardiac pacing pulses.

As was noted above, the ICD circuitry 200, and more specifically, the telemetry I/O circuit 208, transmits data and information to, and receives data and information from, an external communication device. The external communication device allows data and information transmission between the ICD 100 and an external communication system. A functional schematic diagram illustrating this intercommunication functionality is depicted in FIG. 3, and with reference thereto will now be described in more detail.

The intercommunication functionality is implemented via the external communication device 302, which is referred to herein as the communication interface module (CIM) 302. As FIG. 3 depicts, the CIM 302 provides wireless intercommunication between the ICD 100 and a communication system 304, either directly or indirectly via another wireless peripheral device 306. The communication system 304 may be implemented in any one of numerous configurations and may include, for example, one or more of the existing worldwide telephone system (both wired and wireless), the World Wide Web, the Internet, or any one of numerous local area networks (LANs) or wide area networks (WANs). No matter its specific physical implementation, the communication system 304 is configured to wirelessly communicate with the CIM 302, either directly or via the peripheral device 306.

The peripheral device 306 may be any one of numerous wireless communication devices that are configured (or are configurable) to wirelessly communicate with the communication system 304. Some exemplary embodiments include, but are not limited to, a wireless telephone, a cellular telephone, a personal digital assistant (PDA), a personal computer (PC), or a combination thereof, just to name a few. It will additionally be appreciated that the peripheral device 306, no matter its specific physical implementation, is configured (or is configurable) to wirelessly communicate with either, or both, the communication system 304 and the CIM 302 via any one of numerous wireless communication protocols now known or develop in the future. Some non-limiting examples of presently known communication protocols include the various IEEE 802.11 protocols, the BLUETOOTH standard protocol, and the ZigBee Specification protocol, just to name a few.

Figure 3:
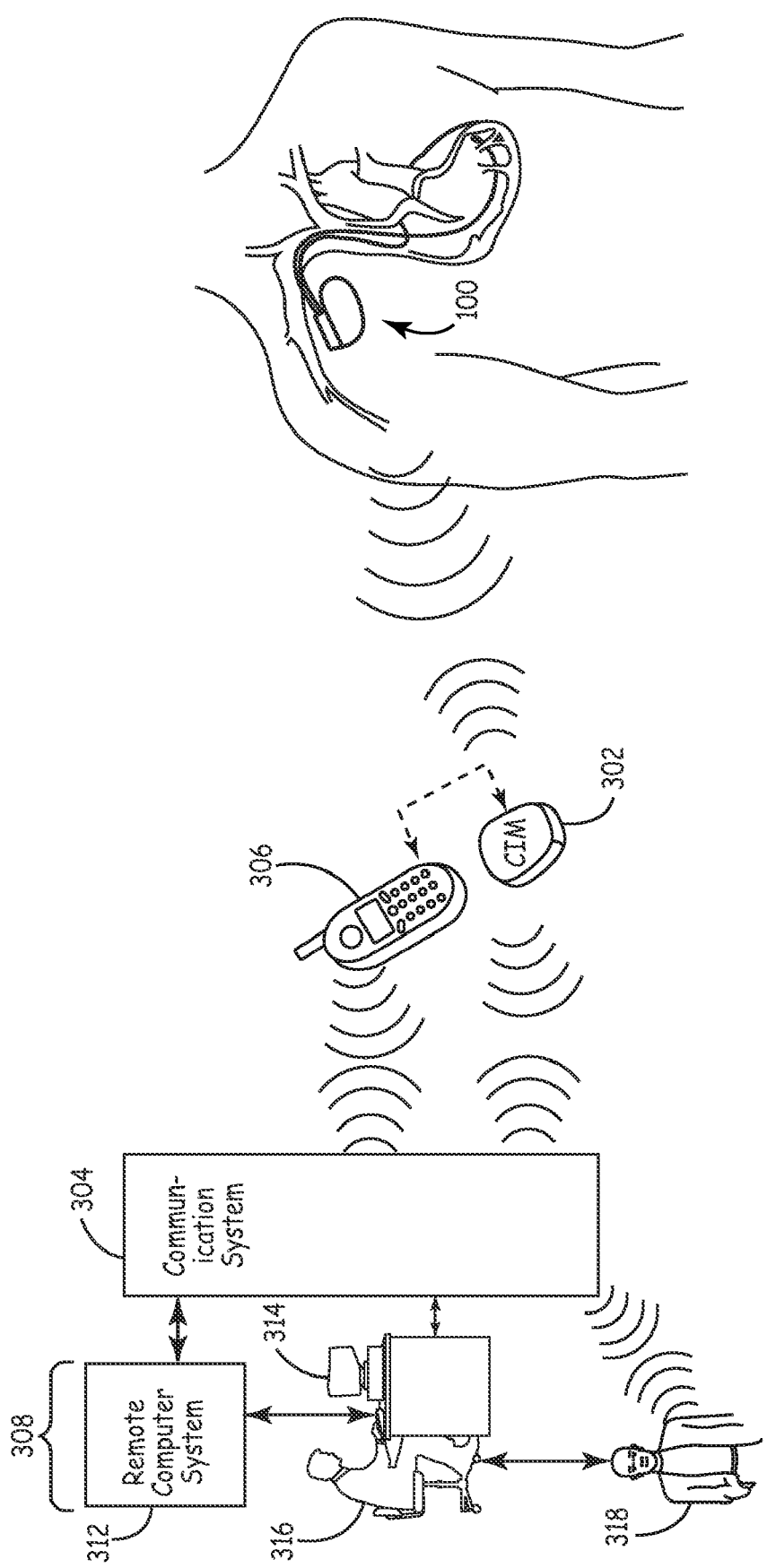
FIG. 3 is a functional block diagram of a communication system according to an embodiment of the present invention.

As FIG. 3 additionally depicts, the communication system 304 facilitates communication with one or more remote systems 308. These remote systems 308 may vary and may include, for example, one or more of a remote computer system 312, one or more remote PCs 314, one or more remote operators 316, and one or more remote health care providers 318. It will be appreciated that the communication system 304 and the remote systems 308 may be configured to allow the remote computer system 312 to communicate directly with the remote operator 316 or remote health care provider 318, or to communicate with the remote operator 316 or remote health care provider 318 via the remote PCs 314. In other embodiments, the communication system can communicate directly with the remote operator 316 or remote health care provider 318, or directly with the remote PCs 314. Moreover, the remote systems 308 may be configured to allow the remote operator 316 to communicate directly with the remote health care provider 318.

Figure 4:
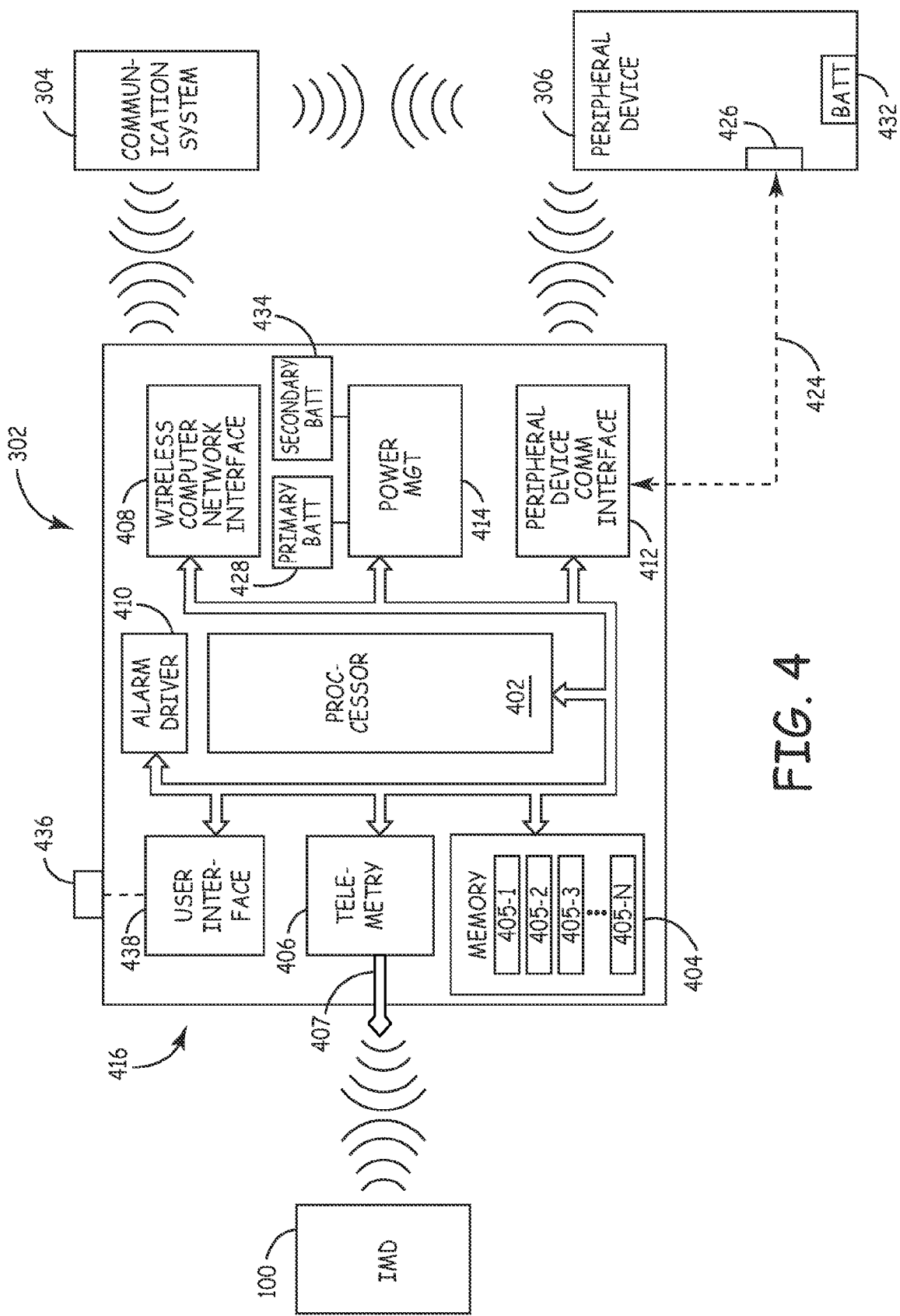
FIG. 4 is a functional block diagram of a communication interface module that may form part of the communication system depicted in FIG. 3.

The CIM 302, as was noted above, is configured to wirelessly communicate with the ICD 100, and to communicate with the communication system 304, either directly or via the peripheral device 306. As FIG. 3 depicts and as will be described further below, direct communication between the CIM 302 and the communication system 304 occurs wirelessly. Moreover, as will also be described further below, communication between the CIM 302 and the peripheral device 306, when used, may occur either wirelessly or via a wired connection, and may occur using any one of numerous communication protocols now known or developed in the future. It will be appreciated that the CIM 302 may be implemented in any one of numerous configurations in order to carry out its functionality. A functional block diagram of one particular physical implementation is depicted in FIG. 4, and with reference thereto will now be described in more detail.

In the depicted embodiment, the CIM 302 includes one or more processors 402 (only one depicted for clarity), memory 404, a telemetry circuit 406, a wireless computer network interface 408, an alarm driver 410, a peripheral device communication interface 412, a power management module 414, and a user interface 416, all in operable communication via a communication bus 422. The processor 402 may include one or more microprocessors, each of which may be any one of numerous known general-purpose microprocessors or application specific processors that operate in response to program instructions. It will be appreciated that this is merely exemplary of one scheme for storing operating system software and software routines, and that various other storage schemes may be implemented. It will also be appreciated that the processor 402 may be implemented using various other circuits, not just one or more programmable processors. For example, digital logic circuits and analog signal processing circuits could also be used.

The memory 404, similar to memory circuit 206 in the ICD circuitry 200, includes a plurality of memory registers 405-1, 405-2, 405-3, . . . 405-N, in which various types of data are stored. The data that may be stored in memory 404 include, but are not limited to, various types of patient-related data and various types of device-related data that are transmitted to the ICM 302 from either, or both, the ICD 100 and the communication system 304. Although depicted as a separate functional block, it will be appreciated that the memory 404 could be integrally formed as part of the processor 402. Moreover, the memory 404 could be physically implemented as any one of numerous types of data storage devices including, for example, a hard disk, or other computer readable medium such as flash memory, ROM, RAM, or EEPROM.

The telemetry circuit 406 is configured to wirelessly communicate with the ICD 100 via RF waves, to thereby transmit data and information to, and to receive data and information from, the ICD 100. As such, the telemetry circuit 406, similar to the telemetry circuit 208 in the ICD circuitry 200, is coupled to an RF antenna 407, and functions as a receiver to receive data or information from the ICD 100, and as a transmitter to transmit data or information to the ICD 100. It will be appreciated that the configuration of the telemetry circuit 406, as either a receiver or a transmitter, is controlled by the processor 402.

The wireless computer network interface 408 is configured to wirelessly communicate directly with the communication system 304. Similar to the peripheral device 306, the wireless computer network interface 408 is configured to wirelessly communicate with the communication system 304 via any one of numerous wireless communication protocols now known or develop in the future. Thus, wireless computer network interface 408 may implement any one or more of the previously-mentioned exemplary communication protocols, such as the various IEEE 802.11 protocols, the BLUE-TOOTH standard protocol, and the ZigBee Specification protocol, just to name a few. It will additionally be appreciated that the wireless communication between the communication system 304 and the wireless computer network interface 408 may occur via RF, optical, or infrared communication.

The wireless computer network interface 408 is further configured to determine communication strength and quality with the communication system 304 and supply data representative of the determined communication strength and quality to the processor 402. The processor 402, in response to these data, determines whether the communication strength and/or quality are too low and, if so, issues a suitable alarm signal to the alarm driver 410. In one embodiment, the processor 402, upon determining that the communication strength and/or quality are too low, additionally places the CIM 302 into a standby mode and/or configures the CIM 302 to limit communications via one or more of the telemetry circuit 406, the wireless computer network interface 408, and the peripheral device communication interface 412.

The alarm driver 410 is configured to receive alarm signals from the processor 402 and, in response to the alarm signals, supplies one or more suitable alarm driver signals to one or more alarm indicators (not shown). The alarm indicators may be implemented using any one, or combination, of numerous types or alarm devices now known or developed in the future including. Some non-limiting examples of alarm devices include one or more visual alarm devices, such as lights, one or more physical alarm devices, such as vibration devices, one or more audible devices, or various combinations of these devices.

The peripheral device communication interface 412 is configured to communicate with the peripheral device 306, when direct intercommunication between the ICM 302 and the communication system 304 is either not possible or not desired. The peripheral device communication interface 412 may be implemented as any one of numerous types of suitable communications interfaces including, for example, any one of numerous types of serial interfaces or parallel interfaces. Moreover, the peripheral communication interface 412 is configured to communicate with the peripheral device either wirelessly or via a wired connection 424 (depicted in phantom in FIG. 4). If the wired connection 424 is used, it will be appreciated that the CIM 302 is configured to mate with the peripheral device 306 via either a standard connector or a manufacturer-specific connector 426 in the peripheral device 306.

The peripheral device communication interface 412, similar to the wireless computer network interface 408, is configured to determine communication strength and quality with the peripheral device 306 and supply data representative of the determined communication strength and quality to the processor 402. The processor 402, in response to these data, determines whether the communication strength and/or quality are too low and, if so, issues a suitable alarm signal to the alarm driver 410. The processor 402, in response to these data, determines whether the connection strength and/or quality are too low and, if so, issues a suitable signal to the alarm driver 410. It will be appreciated that the connection strength and/or quality may, of course, be too low if the peripheral device 306 is turned off. Thus, the peripheral device communication interface 412 is configured to determine when the peripheral device 306 is turned off, and provides data representative of this state to the processor 402. The processor 402, in response, issues a suitable signal to the alarm driver 410.

The peripheral device interface 412 is further configured, based on data received from the peripheral device 306, to determine communication strength and quality between the peripheral device 306 and the communication system 304. The peripheral device interface 412 additionally supplies data representative of the communication strength and quality to the processor 402, which determines whether the communication strength and/or quality is too low and, if so, issues a suitable alarm signal to the alarm driver 410. The peripheral device communication interface 412, together with the CIM telemetry circuit 406 and processor 402, may additionally be configured to automatically turn the peripheral device 306 on if, for example, the CIM 302 receives specified patient- or health-related data from the ICD 100 that needs to be communicated via the peripheral device 306.

The CIM 302 is preferably powered from one or more rechargeable batteries, which may be batteries 428 housed within the CIM 302 itself, batteries 432 that are used to power the peripheral device 306, or both. Although the configuration may vary, the CIM 302 is preferably configured to draw power from the peripheral device batteries 432 when the CIM 302 is coupled to the peripheral device via the wired connection 424, and from the CIM batteries 428 when it is not coupled thereto via the wired connection 424. No matter which set of batteries 428, 432 the CIM 302 is being powered from, it is preferable that the current being drawn therefrom is minimized, and that the patient is made aware if the state of charge of either or both sets of batteries 428, 432 is reduced to a low level state. The power management module 414, which will now be described, facilitates this functionality.

The power management module 414 is configured to minimize current drain from the batteries 428, 432 that are powering the CIM 302, and to preserve a minimum amount of battery charge. To do so, the power management module 414, together with the processor 402, implements wake-up mode and standby mode schemes well known in the implantable medical device and mobile telephone arts. In particular, the power management module 414 is configured to place the CIM 302 in the standby mode, whether it is being power from the CIM batteries 428 or the peripheral device batteries 432, when the CIM 302 has not been communicating with the ICD 100, the communication network 304, and/or the peripheral device 306 for a predetermined time period. In addition, if the CIM 302 is being powered from the peripheral device batteries 432, the power management module 414 is configured to place the peripheral device 306 in the standby mode when the peripheral device 306 has not been used to communicate for a predetermined time period.

In addition to the above, the power management module 414 is further configured to monitor the charge state of either, or both, the CIM batteries 428 and the peripheral device batteries 432 and supply charge-state data representative thereof to the processor 402. In a preferred embodiment, the power management module 414 monitors the state of charge of both batteries 428, 432, no matter which batteries are powering the CIM 302. In response to the charge-state data, the processor 402 determines whether one or both batteries 428, 432 are below a predetermined charge state and, if so, issues a suitable signal to the alarm driver 410. It will be appreciated that the power management module 414, together with the processor 402, may be configured to periodically "wake-up" the CIM 302 and/or peripheral device 306 from the standby mode, when in this mode, to check the state of charge of the batteries 328, 432. The CIM 302 may additionally be configured, during these periodic "wake-ups," to verify communication strength and quality via the wireless communication interface 408 and the peripheral device communication interface 414, as previously described.

In addition to issuing a suitable signal to the alarm driver 410, the processor 402, in one embodiment, will reconfigure the CIM 302 and/or the peripheral device 306 for limited usage. More specifically, if the CIM 302 is being powered from either battery 428, 432 and the processor 402 determines that the battery 428, 432 charge state is below the predetermined charge state, the processor 402 places the CIM 302 into mode in which only limited communications are allowed to occur via the telemetry circuit 406, the wireless computer network interface 408, or the peripheral device communication interface 412. Moreover, if the processor 402 determines that the peripheral device battery 432 charge state is too low, the processor supplies a reconfiguration signal to the peripheral device 306, via the peripheral device communication interface 412, that places the peripheral device 306 in the standby mode and additionally reconfigures it for limited usage. In particular, the peripheral device 306, in response to the reconfiguration signal, reconfigures itself such that it is only able to receive or initiate certain types of communications. For example, if the peripheral device 306 is a cellular phone, it would be reconfigured such that it could only receive calls from, and to initiate calls to, specified telephone numbers. The specified telephone numbers are preferably stored in memory 404 and may be user modifiable. Some examples of the specified telephone numbers include the standard emergency number (e.g., 911), a doctor's telephone number, and a relative's telephone number, just to name a few.

Instead of, or in addition to the above, the peripheral device 306 could be reconfigured in response to the reconfiguration signal such that it could only initiate communication with the communication system 304 if the CIM 302 transmits an override signal, or other specified data, to the peripheral device 306. For example, if the CIM 302 receives specified health-related data from the ICD 100, the CIM 302 could supply an override signal, via the peripheral device communication interface 412, to the peripheral device 306. Alternatively, the peripheral device 306 could be configured to automatically allow communication between itself and the communication system 304 upon receiving specified health-related data transmitted from the CIM 302. It will be appreciated that the functionality described in this paragraph may be implemented whether the peripheral device 306 is a cellular phone, PDA, or other communication device.

In yet another alternative embodiment, the CIM 302 could be implemented with more than one set of batteries. For example, and as depicted in phantom in FIG. 4, the CIM 302 could be implemented with a primary battery 428 and a secondary battery 434. The secondary battery 434 would preferably be used only if the primary battery 428 or the peripheral device battery 432 were unable to power the CIM 302. In addition, the secondary battery 434 preferably would be switched into use, to power either or both the CIM 302 and peripheral device 306, only when either or both devices 302, 306 are needed to communicate with the communication system 304. The power management module 414 and/or the processor 402 would further control the CIM 302 such that charging of the secondary battery 434 takes precedent over charging of the primary battery 428 and/or the peripheral device battery 432. It will be appreciated the CIM 302 may be configured such that battery charging, be it the primary battery 428, the secondary battery 432, or both, could be conducted via a conventional power interface, via a wired communication interface, such as a USB port, or via a wireless communication link.

The user interface 416, which may be implemented as a push-button or toggle-type switch 436 and an appropriate interface circuit 438, is configured to receive user input stimulus, via the switch 436, and supply a signal, via the interface circuit 438, representative thereof to the processor 402. In response, the processor 402 will configure the telemetry circuit 406 to establish communication with, and retrieve data from, the ICD 100 or other implantable medical device within the patient. The processor 402 will additionally configure the wireless computer network interface 408 to transmit the retrieved data to one or more of the remote systems 308 and one or more of the remote operators 316 via the communication system 304. The processor 402 may additionally, or instead, configure the peripheral device communication interface 412 to communicate with the peripheral device 306 and transmit the retrieved data to one or more of the remote systems 308 and one or more of the remote operators 316 via the peripheral device 306.

The user interface 416 allows a patient, or another person, to initiate communication between the CIM 302 and the ICD 100 (or other medical device), and between the CIM 302 and the communication system 304. Thus, if the patient is experiencing certain symptoms that causes the patient to believe he or she is experiencing a condition that should be medically diagnosed, the patient can press or toggle the user interface switch 436 to initiate the above-described intercommunication. It will be appreciated that another person could also press or toggle the user interface switch 436 for the patient if, for example, the patient were unable to do so themselves. The remote operator (or operators) 316 may then analyze the data retrieved from the ICD 100 to determine whether the patient 302 needs further attention. If the determination is that the patient does not need immediate attention, the remote operator 316 can notify the patient, via the communication system 304 and the CIM 302 or peripheral device 306, or both, of this determination. This notification may be made be implemented in any one of numerous forms including, for example, a visual display, an audio signal, or both, that is emitted by the CIM 302, the peripheral device 306, or both. Alternatively, the remote operator 316 could simply place a telephone call to the patient.

If, after analyzing the data, the remote operator 316 determines that the patient may need further attention, the remote operator 316 will determine an appropriate remedial response, and transmit the remedial response to the CIM 302, the peripheral device 306, or both, via the communication system 304. The remedial response may then be transmitted, if appropriate, to the ICD 100. After the remedial response has been delivered, the CIM 302, the peripheral device 306, or both, preferably send a confirmatory message to the remote operator 316 confirming that the remedial response was delivered. It will be appreciated that the remedial response may by any one of numerous types of suitable responses depending, for example, on the data analysis. Some examples of suitable remedial responses include changing one or more operating parameters of ICD 100, commanding the ICD 100 to deliver one or more therapy pulses to the patient (e.g., pace therapy, cardioverter therapy, or defibrillator therapy, or instructing the patient by audio, visual or other means to take action such as, for example, lie down, go to the hospital, call an ambulance, or take a medication.

In addition to the above, the CIM 302 or the peripheral device 306 may be configured to store data concerning patient-initiated events. This allows the stored data to be retrieved and analyzed at a later date so that future remedial responses may be determined, at least partially, on the basis of the data. It will be appreciated that the data may also be stored at the remote data system 130 for later retrieval, analysis and/or future therapy determination.

Figure 5:
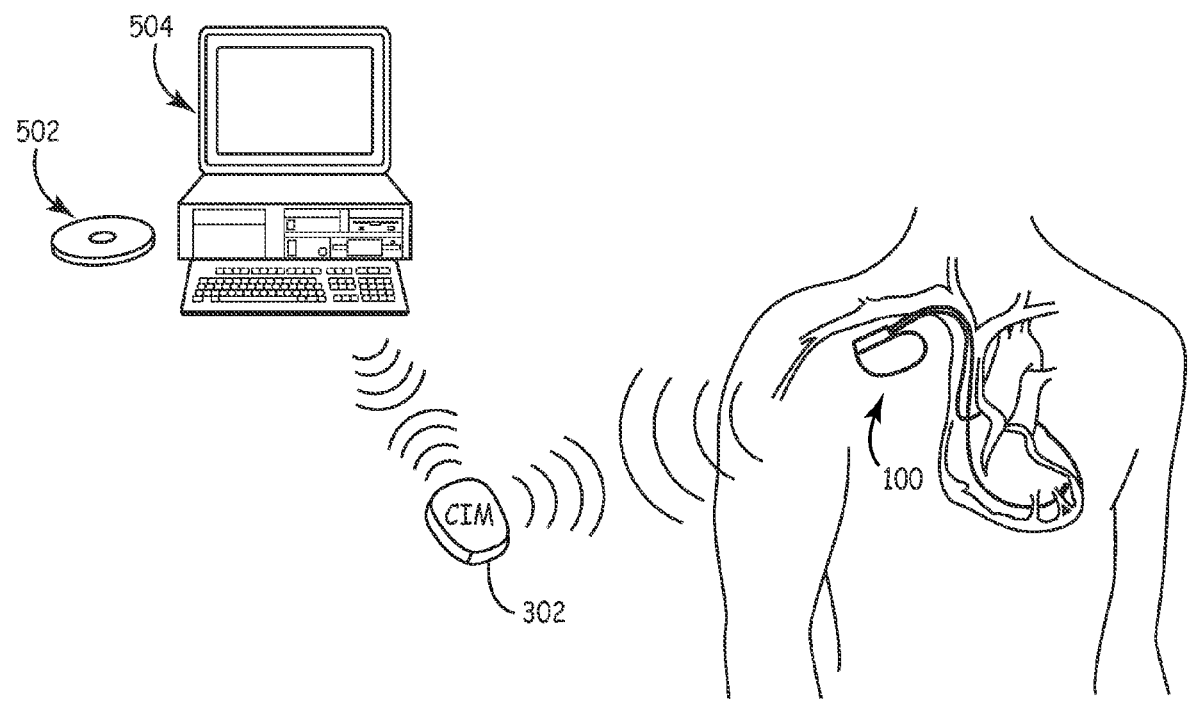
FIG. 5 depicts a software-implemented bio-feedback system for use on a patient personal computer.

With reference now to FIG. 5, in another exemplary embodiment, the patient is additionally be provided with software 502 that is loadable onto a personal computer (PC) 504. The software 502, once loaded on the PC 504, allows the patient to attain certain real-time bio-feedback. In a particular embodiment, if the patient were experiencing specific physical symptoms, such as dizziness, light-headedness, or both, the patient could enter the symptoms into the PC 504. The software 502 may, depending on the symptoms entered by the patient, may request additional patient-related data from the patient. Thereafter, and in response to an additional user input, the software 502 will then command the PC 504 to initiate communication with the ICD 100 via, for example, the CIM 302, to retrieve data from the ICD 100. The communication between the PC 504 and the CIM 302 could occur via either a wireless connection or a wired connection.

No matter the specific manner in which the communication takes place, upon retrieval of the data from the ICD 100, the software 502 will process the retrieved data, the symptom data, and the additional patient-related data to provide the patient with real-time bio-feedback. The feedback may simply be to change certain portions of the patient's diet or medication, or it may request that the patient contact a health professional.

The CIM 302 may be physically implemented according to any one of numerous configurations. For example, the CIM 302 may be implemented as a module that may be worn by the patient and/or be coupled to the peripheral device 306. Alternatively, the CIM 302 may be implemented in a memory module format, which would allow the CIM 302 to readily interface with a memory I/O device of, for example, a personal computer or the peripheral device 306. The memory module format could be in accordance with any one of numerous formats now known, or developed in the future, including, for example, compact flash (CF) memory, secure digital (SD) memory, or a memory stick. In yet another exemplary embodiment, the CIM 302 may be implemented as part of the peripheral device 306 itself.

While an exemplary embodiment(s) has been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide those skilled in the art with a convenient road map for implementing a preferred embodiment of the invention. It being understood that various changes may be made in the function and arrangement of elements described in an exemplary preferred embodiment without departing from the spirit and scope of the invention as set forth in the appended claims.

What is claimed is:

1. A communications device for facilitating communication between a medical device and a wireless communications network, comprising:
    a telemetry circuit configured to wirelessly communicate with one or more medical devices;
    a computer network communication interface configured to wirelessly communicate directly with a wireless computer network;
    a peripheral device communication interface configured to communicate with a wireless peripheral device;
    a processor in operable communication with, and configured to control operations of, the telemetry circuit, the network communication interface, and the peripheral device communication interface;
    a primary battery operable to supply eletrical power to at least the processor, The telemetry circuit, the network communication interface, and the peripheral device Communication interface; and
    a power management module coupled to receive electrical power from the primary battery and configured to determine a state of charge of the primary battery and supply primary battery charge-state data representative thereof;
    wherein the processor receives the primary battery charge-state data and is further configured, upon receipt thereof, to limit communication to or from one or more of the telemetry circuit, the network communication interface, and the peripheral device communication interface if the primary battery charge state is below a predetermined threshold charge state except to predetermined contacts.

2. The device of claim 1, wherein:
    the computer network communication interface includes a configuration to determine communication quality with the wireless computer network and supply data representative thereof to the processor; and
    the processor includes a configuration, in response to the data representative of communication quality, to determine if the communication quality is below a predetermined threshold and, if so, supply an alarm signal.

3. The device of claim 1, wherein:
    the peripheral device communication interface includes a configuration to determine communication quality with the wireless peripheral device and supply data representative thereof to the processor; and the processor is further configured, in response to the data representative of communication quality, to determine if the communication quality is below a predetermined threshold and, if so, supply an alarm signal.

4. The device of claim 3, wherein:
the peripheral device communication interface includes a configuration to determine communication quality between the wireless peripheral device and an external communication system and supply data representative thereof; and
the processor is further configured, in response to the data representative of signal quality, to determine if the communication quality is below a predetermined threshold and, if so, supply an alarm signal.

5. The device of claim 1, wherein the predetermined contacts are emergency support contacts.

6. The device of claim 1, wherein the processor receives the primary battery charge-state data and is further configured, upon receipt thereof, to determine if the primary battery charge state is below a predetermined threshold charge state and, if so, supply an alarm signal.

7. The device of claim 5, wherein the emergency support contacts comprise emergency contact telephone numbers.

8. The device of claim 1, wherein the power management module includes a configuration to determine a state of charge of a peripheral device battery installed in the wireless peripheral device and supply peripheral device battery charge-state data representative thereof.

9. The device of claim 8, wherein the processor receives the peripheral device battery charge-state data and is further configured, upon receipt thereof, to determine if the peripheral device battery charge state is below a predetermined threshold charge state and, if so, supply an alarm signal.

10. The device of claim 8, wherein:
the processor is coupled to receive the peripheral device battery charge-state data and is further configured, upon receipt thereof, to supply a peripheral device reconfiguration signal to the wireless peripheral device, via the peripheral device communication interface, if the peripheral device battery charge state is below a predetermined threshold charge state; and
the wireless peripheral device, upon receipt of the reconfiguration signal, includes a reconfiguration to limit communication to or from itself except to the predetermined contacts.

11. The device of claim 1, further comprising:
a secondary battery operable to selectively supply electrical power to at least the processor, the telemetry circuit, the network communication interface, the peripheral device communication interface, and the power management module.

12. The device of claim 1, further comprising:
a power management module configured to selectively switch at least the processor between a communication mode and a standby mode,
wherein the processor, in the standby mode, draws less electrical power than in the communication mode.

13. The device of claim 12, wherein the power management module, when the processor is in the standby mode, includes a configuration periodically switch the processor from the standby mode to the communication mode and then back to the standby mode.

14. The device of claim 13, wherein:
the processor, when periodically switched into the communication mode from the standby mode, includes a configuration to supply a communication verification signal to the computer network communication interface and the peripheral device communication interface;
the computer network communication interface further configured, in response to the communication verification signal, to determine communication quality with the wireless computer network; and
the peripheral device communication interface further configured, in response to the communication verification signal, to determine communication quality with the wireless peripheral device.

15. The device of claim 1, further comprising:
an alarm driver coupled to receive an alarm signal and operable, in response thereto, to supply an alarm driver signal; and
an alarm indicator coupled to receive the alarm driver signal and operable, in response thereto, to generate an alarm.

16. The device of claim 1, further comprising:
a user interface configured to receive input stimulus from a user and operable, upon receipt of the stimulus, to supply a user interface signal to the processor.

17. The device of claim 16, wherein the processor is further operable, in response to the user interface signal, to configure the telemetry circuit to wirelessly communicate with, and retrieve data from, the medical device.

18. A communications device for facilitating communication between medical device and a wireless communications network, comprising:
a primary battery operable to supply electrical power;
a telemetry circuit coupled to receive electrical power from the primary battery and configured to wirelessly communicate with one or more medical devices;
a computer network communication interface coupled to receive electrical power from the primary battery and configured to wirelessly communicate directly with a wireless computer network;
a peripheral device communication interface coupled to receive electrical power from the primary battery and configured to communicate with a wireless peripheral device;
a power management module coupled to receive electrical power from the primary battery and configured to determine a state of charge of the primary battery and supply primary battery charge-state data representative thereof; and
a processor coupled to receive electrical power from the primary battery and in operable communication with the telemetry circuit, the network communication interface, the peripheral device communication interface, and the power management module, the processor further coupled to receive the primary battery charge-state data and configured, upon receipt thereof, to limit communication to or from one or more of the telemetry circuit, the network communication interface, and the peripheral device communication interface if the primary battery charge state is below a predetermined threshold charge state except to predetermined contacts.

19. The device of claim 18, wherein:
the power management module further includes a configuration to determine a state of charge of a peripheral device battery installed in the wireless peripheral device and supply peripheral device battery charge-state data representative thereof;
the processor is coupled to receive the peripheral device battery charge-state data and is further configured, upon receipt thereof, to supply a peripheral device reconfiguration signal to the wireless peripheral device, via the peripheral device communication interface, if the peripheral device battery charge state is below a predetermined threshold charge state; and the wireless peripheral device, upon receipt of the reconfiguration signal, is reconfigured to limit communication to or from itself except to predetermined contacts.

20. The device of claim 18, wherein the predetermined contacts are emergency support contacts.

21. The device of claim 20, wherein the emergency support contacts comprise emergency contact telephone numbers.

22. A communication device for facilitating communication between one or more medical devices and a wireless communications network, the communication device comprising:

a telemetry circuit configured to wirelessly communicate directly with one or more medical devices;

a first communication interface configured to wirelessly communicate directly with the wireless communication network;

a second communication interface configured to communicate with a wireless peripheral device;

a processor; and a battery operable to supply electrical power to at least the processor, the telemetry circuit, the first communication interface, and the second communication interface, wherein the processor is configured to communicate with and control operations of the telemetry circuit, the first communication interface, and the second communication interface, determine a charge state of the battery and, if the charge state of the battery is below a predetermined threshold, limit communication to or from one or more of the telemetry circuit, the first communication interface and the second communication interface except to predetermined contacts and supply an alarm signal.

* * * * *